United States Patent [19]

Bazile et al.

[11] 4,219,482

[45] Aug. 26, 1980

[54] PROCESS FOR PREPARING THIOPHENE AND FURAN DERIVATIVES

[75] Inventors: Yves Bazile; Paul de Cointet de Fillain, both of Sisteron; Charles Pigerol, Saint-Ouen, all of France

[73] Assignee: Labaz, Paris, France

[21] Appl. No.: 960,563

[22] Filed: Nov. 14, 1978

[30] Foreign Application Priority Data

Nov. 11, 1977 [FR] France ................. 77 34553

[51] Int. Cl.$^2$ ................. C07D 333/42; C07D 333/44; C07D 307/70; C07D 307/71
[52] U.S. Cl. ................. 549/68 A; 260/347.5
[58] Field of Search ................. 260/332.26, 347.5; 549/68

[56] References Cited

U.S. PATENT DOCUMENTS 3,733,319   5/1973   Henry ................. 260/240

FOREIGN PATENT DOCUMENTS 116452  11/1975  Fed. Rep. of Germany ...... 260/332.26
908023   4/1954  Fed. Rep. of Germany ...... 260/332.26

Primary Examiner—Robert Gerstl
Attorney, Agent, or Firm—Mason, Kolehmainen, Rathburn & Wyss

[57] ABSTRACT

A process for preparing methyl-nitrothenoate and methyl-nitrofuroate by oxidation of the corresponding aldehyde is described.

7 Claims, No Drawings

PROCESS FOR PREPARING THIOPHENE AND FURAN DERIVATIVES

The present invention relates to a process for preparing thiophene and furan derivatives and also to the derivatives obtained by the said process.

The invention relates more particularly to a process for the preparation of nitrated derivatives of the general formula:

   I in which X represents an oxygen or sulphur atom.

The esters represented by formula I are known products having been published, for instance, in Chemical Abstracts 44, 1543 i, 44, 6474 i or 59, 12741 b with the exception of methyl 4-nitro-2-furoate.

No trace of this compound has, in fact, been found in the chemical literature. Yet another object of the invention therefore concerns methyl 4-nitro-2-furoate as a novel industrial product.

The compounds of formula I are particularly valuable for preparing products having pharmacological properties and more especially antiparasitic properties.

The methods described in the chemical literature regarding the preparation of esters of formula I starting from the corresponding aldehydes are essentially designed for laboratory use.

For example, a process for preparing methyl 5-nitro-thenoate is described in J.A.C.S., 74, 1356–1357 (1952) by oxidation of 5-nitro-2-formyl-thiophene by means of potassium permanganate.

Likewise, a process for the preparation of methyl 4-nitro-2-thenoate is given in Chemical Abstracts 59, 12741 b that consists in oxidizing 4-nitro-3-bromo-2-formyl-thiophene by means of chromous anhydride, esterifying the acid so formed and then dehalogenating, in the presence of copper powder, to provide the required ester.

Other methods involve the oxidation of the appropriate aldehydes with sodium bichromate in sulphuric acid medium and then the esterification of the acid formed.

These various methods are essentially characterized by a relatively large number of steps of preparation, by the employment of expensive reagents and by the use of catalysts that it would be preferable to avoid as far as possible.

The need for finding an industrial process for obtaining the esters of formula I are thus of paramount importance.

Up to present, the synthesis of aromatic esters by oxidation of aldehydes and esterification in the same reaction medium has been performed by using organic hypohalides as oxidation agents.

Such a method involving the use of tert-butyl hypoiodite is described in J. Chem. Soc., Perkin Trans. I, 383–386 (1976).

In accordance with this method, the aldehyde is added to tert-butyl hypoiodite formed from tert-butyl hypochlorite, iodine and potassium tert-butoxide in tert-butanol as medium.

In this way, 4-nitro-benzaldehyde reacts with tert-butanol in the presence of tert-butyl hypiodite to give tert-butyl 4-nitro-benzoate.

The preparation of the compounds of formula I by introducing 4-nitro- or 5-nitro-2-formyl-thiophene or -furan into a reaction medium, as suggested by the reference cited hereabove, is to be avoided on the industrial scale.

The aldehydes in question present, in fact, a high level of toxicity creating for the operators acute problems of cutaneous allergy.

As a result of this high degree of toxicity, the handling of these aldehydes must be reduced to the minimum, particularly on the industrial scale, which consequently abviates all possibility of purification of these products.

It is therefore essential that a process be found for preparing the compounds of formula I starting from the aldehydes cited above, which has the following qualities:

simplicity as regards procedure
use of the aldehydes with the minimum of manipulation, for instance by avoiding the need for purification and introduction into a reaction medium
high yield
production cost as low as possible.

For this purpose, attempts have been made to use the method described in U.S. Pat. No. 116,452 of the German Democratic Republic.

This Patent teachs, more particularly, the preparation of methyl benzoate starting from benzaldehyde in methanol to which an aqueous solution of sodium hydroxide is first added followed by bromine.

Trials carried out within the scope of the present invention have shown that this method may very well be applied to the production of a nitrated aromatic derivative i.e. methyl 4-nitro-benzoate.

In fact, in accordance with this process, pure methyl 4nitro-benzoate was obtained in a yield of 88.5% starting from 0.1 mol of 4-nitro-benzaldehyde, 0.12 mol of bromine, 100 ml of methanol and 0.24 mol of sodium hydroxide.

On the other hand, under the same operating conditions and starting from the same amounts of 4-nitro-2-formyl-thiophene or 5-nitro-2-formylfuran and the same amounts of methanol, bromine and sodium hydroxide as those given above, neither methyl 4-nitro-2-thenoate nor methyl 5-nitro-2-furoate could be obtained.

It has now been found, in accordance with the present invention, that it is nevertheless possible to obtain the compounds of formula I starting from a halogen, an alkali metal hydroxide and 4-nitro- or 5-nitro-2-formyl-thiophene or -furan without having to introduce these aldehydes into the reaction medium.

In accordance with one aspect of the process of the invention, an alkali metal hydroxide, for example sodium hydroxide, is introduced into a reaction medium formed by adding a halogen such as chlorine, bromine or iodine to a methanolic solution of 4-nitro- or 5-nitro-2-formylthiophene or -furan.

The introduction of the alkali metal hydroxide will start at 10° C. while the oxidation reaction itself will take place at a temperature between 10° C. and the reflux temperature of the methanol.

In this way, methyl 5-nitro-2-thenoate was obtained in a yield of 96.5% in crude product and 83% in pure product starting from 0.1 mol of 5-nitro-2-formyl-thiophene, 0.12 mol of bromine, 100 ml of methanol and 0.24 mol of sodium hydroxide.

Furthermore, it has been found, in accordance with a second aspect of the invention, that the esters of formula I can be prepared by adding a halogen to a methanolic solution of the corresponding aldehyde. Thus, in accordance with an alternative procedure of the invention, a halogen, for example chlorine, bromine or iodine is introduced into a reaction medium formed by adding an alkali metal carbonate, an alkali metal bicarbonate or an alkali metal acetate/acetic acid mixture to a methanolic solution of 4-nitro- or 5-nitro-2-formyl-thiophene or -furan.

The introduction of the halogen will start at the temperature of 0° C. while the reaction will preferably take place at a temperature between 0° C. and the reflux temperature of the methanol.

Under these operating conditions, the methyl esters of formula I were obtained in yields superior to 80% in pure product. This second aspect of the process of the invention is very surprising. In the same conditions of temperature and introduction of the reagents but starting from tert-butanol, isopropanol or ethanol as esterifying agents with a view to preparing the ter-butyl, isopropyl and ethyl esters, quite different results were, in fact, obtained from those obtained in methanol with a view to preparing the methyl esters of formula I.

For example, only 40% of tert-butyl 5-nitro-2-thenoate and 5 to 10% of ethyl 5-nitro-2-thenoate were obtained, starting from 5-nitro-2-formylthiophene and tert-butanol or ethanol respectively. In isopropanol, the yield in isopropyl 5-nitro-2-thenoate was nil starting from 5-nitro-2-formyl-thiophene.

An additional trial performed under the same operating conditions but in tert-butanol with another nitrated aromatic aldehyde i.e. 4-nitrobenzaldehyde provided tert-butyl 4-nitro-benzoate in a yield of only 13.5%.

Taking into account the various aspects of the invention indicated hereabove, the methyl esters of formula I will be prepared, in accordance with the novel process, by reacting a halogen and an aldehyde of the general formula:

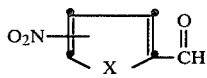

II in which X has the same meaning as in formula I, the said reaction consisting in introducing into a methanolic solution of the aldehyde of formula II:
either the halogen and then an alkali metal hydroxide or an alkali metal carbonate, an alkali metal bicarbonate or an alkali metal acetate/acetic acid mixture and then the halogen.

As indicated above with respect to each aspect of the process of the invention, the halogen will be for example chlorine, bromine or iodine and preferably bromine.

The alkali metal will be for example sodium while the reaction itself will take place at a temperature between 0° C. and the reflux temperature of the methanol.

The compounds of formula II are known products.

From the overall results listed above, it is clear that the process of the invention offers an undoubted advantage over the processes suggested by the prior art.

The two procedures for using the reagents which, taken together, constitute the process of the invention appear to be equal to each other with respect to the yield in methyl esters of formula I. This is certainly not the case when the process of the Patent of the German Democratic Republic cited above is used.

Furthermore, the process of the invention has proved to be superior to the known processes used for preparing the esters of formula I.

The process of the invention is, in fact, perfectly adapted for use on the industrial scale. Furthermore, it only involves the use of inexpensive reagents and avoids the utilization of catalysts.

The non-limitative Examples which follow illustrate the process of the invention:

EXAMPLE 1

Preparation of methyl 5-nitro-2-thenoate

Into a 250-ml flask equipped with a central stirrer, a thermometer and a condenser and containing 15.7 g (0.1 mol) of 5-nitro-2-formylthiophene, were introduced 21 g (0.25 mol) of sodium bicarbonate and 100 ml of pure methanol.

Through a dip tube, 8.5 g (0.12 mol) of chlorine were added to the reaction medium at the temperature of 0° C. The introduction of chlorine was terminated after 45 minutes and then the mixture was maintained at the reflux temperature of the methanol for 2 hours until it became totally discoloured. The reaction medium was then poured into water and extracted with ethyl ether. The ethereal phase was washed with water, dried on sodium sulphate and heated to dryness in a rotatory evaporator. The crude solid so obtained was recrystallized from a 70/30 heptane/1,2-dichloro-ethane mixture and then brought to 0° C.

In this manner, 18 g of crude methyl 5-nitro-2-thenoate were obtained which represents a yield of 96.5%.

Weight of pure ester obtained: 15.5 g which represents a yield of 83%.

M.P.: 75° C.

EXAMPLE 2

Preparation of methyl 5-nitro-2-thenoate

Into a 250-ml flask equipped with a central stirrer, a thermometer and a condenser and containing 15.7 g (0.1 mol) of 5-nitro-2-formylthiophene, were introduced 21 g (0.25 mol) of sodium bicarbonate and 100 ml of methanol. Through a dropping-funnel, 19.2 g (0.12 mol) of bromine were added, in 30 minutes, to the reaction medium at the temperature of 0° C. Reflux was maintained for one hour until the medium became totally discoloured.

The reaction medium was then poured into water and extracted with ethyl ether. The ethereal phase was washed with water, dried on sodium sulphate and heated to dryness in a rotatory evaporator. The crude solid so obtained was recrystallized from a 70/30 heptane/1,2-dichloro-ethane mixture and then brought to 0° C.

In this manner, 18 g of crude methyl 5-nitro-2-thenoate were obtained, which represents a yield of 96.5%.

Weight in pure ester obtained: 15.5 g which represents a yield of 83%.

M.P.: 76° C.

Following the same method as that described above but starting from the appropriate products, the following compounds were prepared:

Compound (a) Methyl 4-nitro-2-thenoate
Weight in crude ester obtained: 18 g which represents a yield of 96.5%.

Weight in pure ester obtained: 15.5 g which represents a yield of 83%.

M.P.: 101° C.

(b) Methyl 5-nitro-2-furoate

Weight in crude ester obtained: 16.4 g which represents a yield of 96%.

Weight in pure ester obtained: 15 g which represents a yield of 88%.

M.P.: 78° C.

(c) Methyl 4-nitro-2-furoate.

EXAMPLE 3

Preparation of methyl 5-nitro-2-thenoate

Into a 250-ml flask fitted with a central stirrer, a thermometer and a condenser and containing 15.7 g (0.1 mol) of 5-nitro-2-formylthiophene, were introduced 21 g (0.25 mol) of sodium bicarbonate and 100 ml of pure methanol. By small portions, 30.5 g (0.12 mol) of iodine were added to the reaction medium at the temperature of 0° C. The operation of addition lasted one hour. After that, the medium was maintained at the reflux temperature of the methanol for 2 hours until it became totally discoloured and then it was poured into water and extracted with ethyl ether. The ethereal phase was washed with water, dried on sodium sulphate and heated to dryness in a rotatory evaporator.

The crude solid so obtained was recristallized from a 70/30 heptane/1,2-dichloro-ethane mixture and then brought to 0° C.

In this manner, 18 g of crude methyl 5-nitro-2-thenoate were obtained which represents a yield of 96.5%.

M.P.: 74° C.

EXAMPLE 4

Preparation of methyl 5-nitro-2-thenoate

Into a 250-ml flask fitted with a central stirrer, a thermometer, a condenser and a dropping-funnel and containing 15.7 g (0.1 mol) of 5-nitro-2-formyl-thiophene, were introduced 16 g (0.15 mol) of dry sodium carbonate together with 100 ml of pure methanol. The mixture was heated to 40° C. As soon as this temperature was reached, 19.2 g (0.12 mol) of bromine were added in 30 minutes. The reaction medium was maintained for one hour at the reflux temperature of the methanol, was poured into water and then extracted with ether. The ethereal phase was washed with water dried on sodium sulphate and heated to dryness in a rotatory evaporator. The crude solid obtained was recrystallized from a 70/30 heptane/1,2-dichloro-ethane mixture and then brought to 0° C.

In this manner, 18 g of crude methyl 5-nitro-2-thenoate were obtained which represents a yield of 96.5%.

Weight of pure ester obtained: 15.5 g which represents a yield of 83%.

M.P.: 75° C.

EXAMPLE 5

Preparation of methyl 5-nitro-2-thenoate

Into a 250-ml flask equipped with a central stirrer, a thermometer, a condenser and a dropping-funnel and containing 15.7 g (0.1 mol) of 5-nitro-2-formyl-thiophene, were introduced 100 ml of methanol. The medium was cooled to 10° C. and 19.2 g (0.12 mol) of bromine were added in one operation. After that, 9.6 g (0.24 mol) of powdered sodium hydroxide were introduced in 30 minutes. The medium was allowed to react for 30 minutes at room-temperature and then for 30 minutes at the reflux temperature of the methanol. The reaction medium was then poured into water and extracted with ethyl ether. The ethereal phase was washed with water, dried on sodium sulphate and heated to dryness in a rotatory evaporator.

The crude solid so obtained was then recrystallized from a 70/30 heptane/1,2-dichloro-ethane mixture and then brought to 0° C.

In this manner, 18 g of crude methyl 5-nitro-2-thenoate were obtained which represents a yield of 96.5%.

Weight in pure ester obtained: 15.5 g which represents a yield of 83%.

M.P.: 74° C.

What we claim is:

1. Process for preparing nitrated derivatives of the general formula:

in which X represents an oxygen or sulphur atom, by the reaction involving the addition of a halogen to a methanolic solution of a base and of an aldehyde of the general formula:

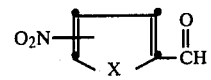

in which X has the same meaning as given above, the reaction taking place between 0° C. and reflux temperature of the reaction mixture, wherein the base is an alkali metal carbonate or bicarbonate.

2. Process according to claim 1 whereby the halogen is chlorine, bromine or iodine.

3. Process according to claim 1 wherein the alkali metal is sodium.

4. Proces according to claim 1 wherein X is sulfur and the nitro substituent is located in the 5-position on the ring.

5. Process according to claim 1 wherein X is sulfur and the nitro substituent is located in the 4-position on the ring.

6. Process according to claim 1 wherein X is oxygen and the nitro substituent is located in the 5-position on the ring.

7. Process according to claim 1 wherein X is oxygen and the nitro substituent is located in the 4-position on the ring.

* * * * *